United States Patent [19]

Bohl et al.

[11] 4,051,731
[45] Oct. 4, 1977

[54] FLUID SAMPLING SYSTEM

[75] Inventors: Thomas L. Bohl, Madison; Leonard J. Visdos, Lyndhurst, both of Ohio

[73] Assignee: Bailey Meter Company, Wickliffe, Ohio

[21] Appl. No.: 755,720

[22] Filed: Dec. 30, 1976

[51] Int. Cl.² ............................................. G01N 1/16
[52] U.S. Cl. .................................................. 73/422 R
[58] Field of Search ........... 73/421 B, 422 R, 421.5 R

[56] References Cited
U.S. PATENT DOCUMENTS

| 2,030,682 | 2/1936 | Campbell | 73/422 R |
| 2,534,181 | 12/1950 | Roberts | 73/422 R |
| 2,675,706 | 4/1954 | Edgar | 73/421 B |

Primary Examiner—S. Clement Swisher

Attorney, Agent, or Firm—Vytas R. Matas; Joseph M. Maguire

[57] ABSTRACT

A fluid sampling system has a series of sample probes having inlets located at different positions across a fluid conveying duct. The outlets of all the sample probes are connected to a valve assembly. Each of the sample probes is made to have substantially the same length and diameter to provide equivalent transport times and volumes to fluids sampled from the various locations. The valve assembly allows selective connection of the sample probes to the fluid analyzer allowing either individual sample probes to be connected to the analyzer to determine local duct conditions or the connection of all the sample probes to the analyzer to determine the average duct condition.

9 Claims, 5 Drawing Figures

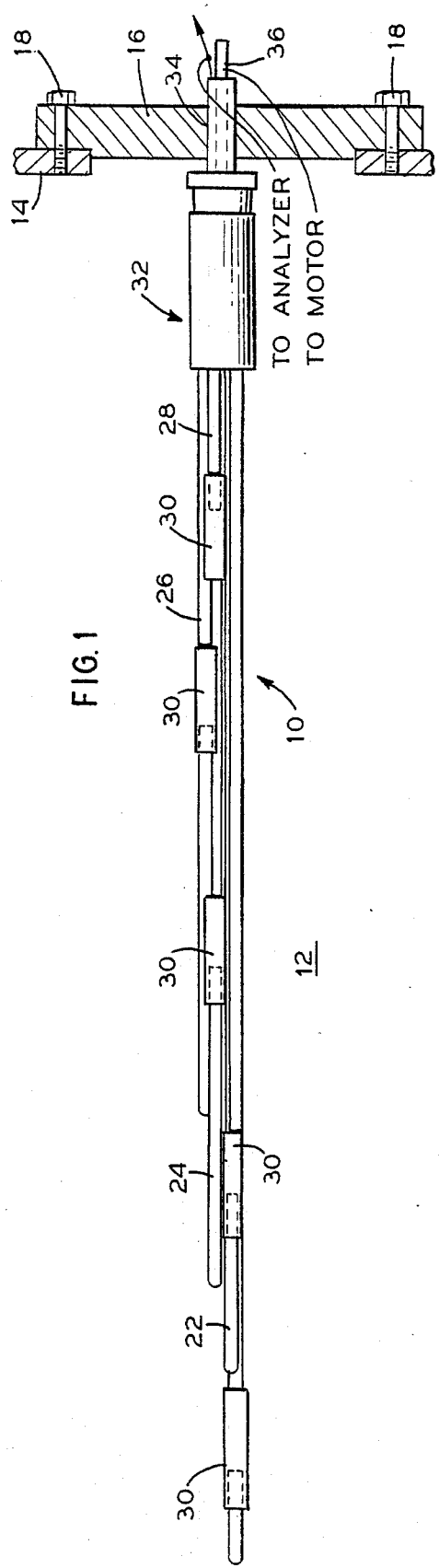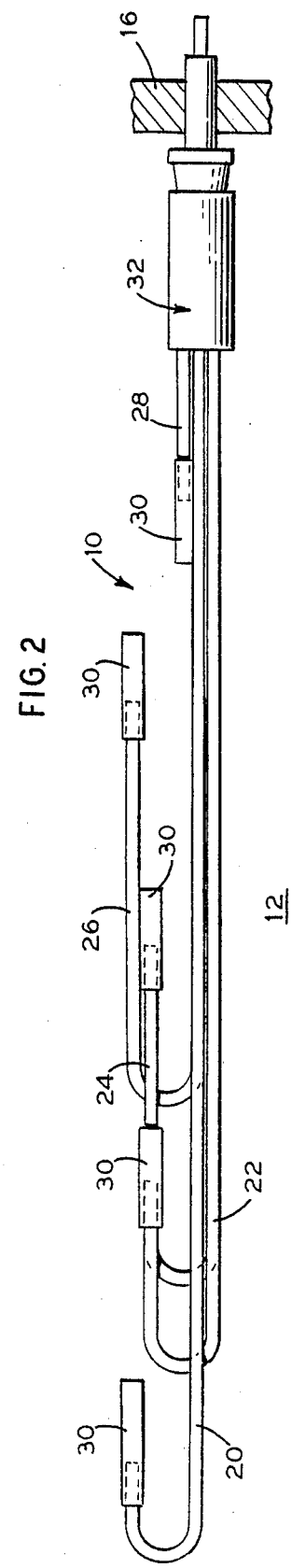

FLUID SAMPLING SYSTEM

BACKGROUND OF THE INVENTION

1. Field of the Invention

The present invention generally relates to fluid sampling systems and particularly to such systems having a plurality of different sample probes which are selectively connectable to a fluid analyzer.

2. Description of the Prior Art

Fluids moving in ducts and pipes with no obstructions have laminar flow if the Reynolds Number is less than 2,000. Under such conditions stratification of the fluid occurs across the duct or pipe area. Thus, a sample taken at one point in the duct may be of considerably different composition than a sample taken at another point in the duct.

In order to obtain a representative sample of the fluid passing through the duct or pipe, it is known to insert sample probes at various points across the duct. Examples of such a placement of sample probes at different points in the duct may be found in U.S. Pat. No. 3,736,792 issued June 5, 1973 to Stephen D. Poulsen and U.S. Pat. No. 3,780,566 issued Dec. 25, 1973 to Kenneth Burton Smith et al. In such known set-ups although the diameters of the sample probes are approximately equal and equal volumes of fluid enter the sample probes, since the distance from the inlet of the sample probe to the exhaust of the probe are not equal thorough sampling for averaging purposes is not accomplished since the fluid entering the farthest inlet of the sample probes will not reach the outlet of that sample probe at the same time as fluid entering the shorter inlet to outlet sample probes. Therefore, the composite of the fluids exhausted from the various sample probes is not a true representation of the fluid flowing across the pipe at any given instant and does not provide a true average of such.

The diameters of the various probes could be sized so that the fluid transport times from each sample probe would be equal. However, then the volume of fluid entering each sample probe would not be equal and the composite sample from all the probes would again not be a true average but would be biased towards the fluid entering the larger diameter probes. An example of such a system using variable diameter inlets may be found in U.S. Pat. No. 3,777,571 issued Dec. 11, 1973 to Erich Jaeger.

SUMMARY OF THE INVENTION

The present invention solves the problems associated with the known prior art devices as well as others by providing a fluid sampling system having a plurality of sample probes which provide substantially identical fluid transport times and volumes to samples taken from each of the sample probes.

To accomplish this the sample probes are made to be of substantially identical length by taking sample probes of the length of the individual sample probe to provide inlets at various distances along the duct. As such each sample of fluid taken at different points across the duct must travel the identical length of sample probe resulting in substantially identical transport times between the inlets and outlets of the sample probes. As such the outlets of the sample probes may be manifolded and are easily averaged to provide a true average of the fluid conditions along the duct at any particular instant of time.

To allow sampling of individual sample probes as well as averaging the outputs of the plurality of the sample probes a valve means is connected to the plurality of the sample probes. The valve means includes a stator or manifold into which the plurality of sample probes are sealably connected along a predetermined diameter. A rotor is mounted proximately to the stator which has a single passageway rotatably alignable with the individual sample probe outlet. Thus, when the rotor is sealably connected to the stator, rotation of the rotor to predetermined angles will allow only the outlets of individual sample probes to pass through the rotor. The rotor may also be backed away from the stator to allow all of the outlets of all of the sample probes to exhaust into a space between the rotor and the stator to allow the outlets of all of the sample probes to pass through and around the rotor. This then allows an average of all of the sample probe samples.

From the foregoing it will be seen that one aspect of the present invention is to provide a plurality of sample probes which will have substantially identical transport times for samples taken at different points of a duct.

Another aspect of the present invention is to provide a fluid sampling system which will allow individual sampling of a plurality of sample probes as well as an average of the samples taken from all of the sample probes at a particular instant of time.

These and other aspects of the present invention will be more fully understood upon due consideration of the following description of the preferred embodiment and the accompanying drawing.

BRIEF DESCRIPTION OF THE DRAWINGS

FIG. 1 depicts a side view of the fluid sampling system of the present invention mounted in a duct.

FIG. 2 is a top view of the FIG. 1 system.

DESCRIPTION OF THE PREFERRED EMBODIMENTS

Figure 3:
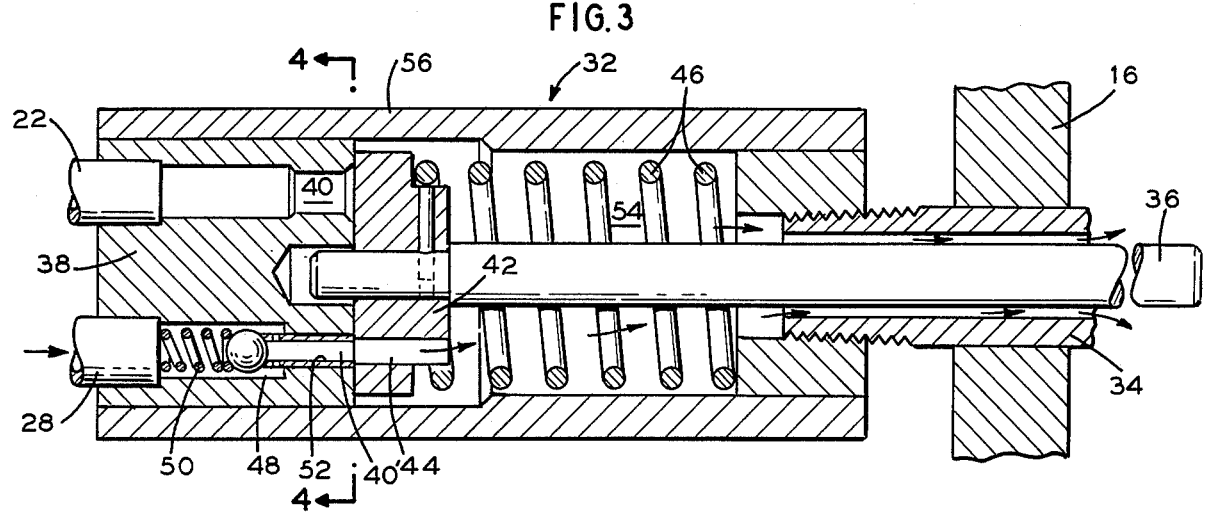
FIG. 3 is an expanded cross-section of the valve mechanism of the FIG. 1 embodiment.

Referring now to the drawings it will be understood that the showings therein are intended to describe a particular preferred embodiment and are not intended to limit the invention thereto. With particular reference to FIGS. 1 and 2 it may be seen that a fluid sampling system 10 is shown mounted inside of a duct 12 through which sample gases are flowing. These sample gases are the products of combustion and the quality of the combustion process may be determined by the sampling of these gases. Since stratification occurs in the duct, samples are needed from various positions across the duct to determine the condition of the sample gases across the duct. The fluid sample system 10 is mounted to a duct wall 14 by first mounting the fluid sample system 10 to a plate 16 which is in turn bolted to the duct wall 14 through bolts 18 to seal the fluid sampling system inside the duct 12.

The fluid sampling system 10 includes a plurality of fluid sample probes. In this particular instance 5 sample probes 20, 22, 24, 26, and 28 are disclosed although it will be understood that any number greater or less may also be used. The inlet of each probe 20, 22, 24, 26, and 28 is capped with a 20 micron-metal mesh filter 30 which prevents particles from entering the sample probes and clogging them thereby. The outlet of all the sample probes, 20, 22, 24, 26 and 28 terminate in a valve assembly 32 which is also mounted inside the duct 12. The valve assembly 32 is threaded onto a pipe nipple 34 which extends through the plate 16 and allows a rotor shaft 36, whose function will be described later, to extend externally of the duct 12 through the pipe nipple 34.

Sample probes 20, 22, 24, and 26 are all made from .250 inch OD stainless steel tubing of substantially identical length and inside diameter to provide identical transport time and volume to samples taken at the inlet 30 of each of these probes 20, 22, 24, and 26 and to the outlets of these probes 20, 22, 24, and 26 terminating in the valve assembly 32. However, to allow different points of the duct 12 to be sensed by the individual sample probes 20, 22, 24, and 26 a 180° bend is made at different lengths of the sample probes 20, 22, 24, and 26 to have the inlets 30 be located at different points of the duct 12. Since each of the sample probes 20, 22, 24, and 26 have the identical 180° bend the resistance of each sample probe 20, 22, 24, and 26 is still maintained substantially identical and does not cause any variation in the transport time or volume of the probe.

The sample probe 28 is a short length of unbent stainless tube which is purposely not bent or matched to the sample probes 20, 22, 24, and 26 since it serves a function different than that of the sample probes 20, 22, 24, and 26. More specifically, the sample probe 28 is intended to check the oxygen level of the duct proximately to the wall 14 to provide an indication of any leakage through the duct wall 14 into the duct 12. As such the sample from the sample probe 28 is always taken individually and does not become involved in any averaging of the duct 12 condition. Thus there is no need to attempt a matching of the sample probe 28 to the samples 20, 22, 24, and 26 and its smaller size is due to economic and functional considerations.

The valve assembly 32 allows individual sampling of the sample probes 20, 22, 24 and 26 and 28 or an average sampling of the probes 20, 22, 24, and 26 to be effected in a manner that will be described later. In any event whether the sampling is indiviaul or averaged the fluid from the sample probes 20, 22, 24, 26 and 28 is passed through the nipple 34 around the rotor shaft 36 and out of the duct 12. This sample fluid is then directed to a fluid analyzer such as a gas analyzer described in U.S. Pat. No. 3,960,500 entitled "Gas Analyzer System." The connection to such an analyzer may be made by threading a pipe to the nipple 34 which will allow the fluids to flow to the analyzer and which will sealably allow rotation of the rotor shaft 36 by a connection to a rotor motor (not shown).

Figure 4:
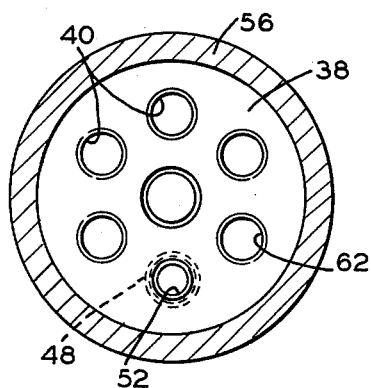
FIG. 4 is an end view of the stator of the valve mechanism of FIG. 3 taken along section 4—4 of FIG. 3.

Turning now to FIG. 3 and 4 it will be seen that the sample probes 20, 22, 24, 26 and 28 are manifolded into a stator 38 so as to be located along a predetermined diameter at predetermined angles. The stator 38 has passageways 40 and 40' extending therethrough which allow fluids sampled by the individual sample probes 20, 22, 24, 26 and 28 to be transmitted through the stator 38. Mounted against the face of the stator 38 is a rotor 42 having a single passageway 44 located along a diameter substantially identical to the diameter of the stator 38 which locates the passageways 40. The rotor 42 is spring loaded against the face of the stator 38 by a spring 46 to seal off all the passagways 40 and 40' with the exception of any passageway 40 or 40' which is aligned with the passageway 44.

As was mentioned earlier, the sample probe 28 is uniquely constructed for a unique function and the output therefrom is not intended to be used in any sample averaging. To insure that the output from this sample probe 28 will be closed at all times except when its individual output is required, a ball valve 48 is located between the passageway 40' and the outlet of the sample probe 28. The ball valve 48 is spring loaded by a spring 50 to seal the passageway 40'. A slide tube 52 is located against the ball valve 48 which normally protrudes out of the face of the stator 38 when the rotor 42 is backed away from the stator 38. Thus the spring 50 forces the ball valve 48 to block the passageway 40'. Whenever the rotor 42 is pressed against the stator 38 the slide tube 52 is pushed against the ball valve 48 allowing fluid to flow around it and into the passageway 44. Thus if the passageway 44 is aligned with the passageway 40' connected to the sample probe 28, fluid from the sample probe 28 flows into a chamber 54 formed by the housing 56 and from this chamber 54 around the annulus of the rotor shaft 36 and out of the duct 12. If the passageway 44 is aligned with any other passageway 40 flow is blocked from the sample probe 28 by the solid face of the rotor 42 even though the ball vlave 48 is opened by the slide tube 52.

The remaining passageways 40 have no such ball valves and are individually exhausted by aligning the passageway 44 with individual passageways 40. The solid face of the rotor 42 blocks all the remaining passageways 40. The flow through the aligned passageways is again into the chamber 54 and out around the annulus of the rotor shaft 36, as was described earlier.

Angular rotations of the rotor shaft are effected by a motor (not shown) which is stepped to have predetermined known spots which will align the passageway 44 with the individual passageways 40 to allow known individual sampling of the sample probes 20, 22, 24, 26 and 28. To allow averaging of the samples taken by sample probes 20, 22, 24, and 26 the motor (not shown) is also provided with a known position which will allow retraction of the rotor 42 against the force of the spring 46 from the face of the stator 38. All of the passageways 40 are now able to eject the samples sensed by the sample tubes 20, 22, 24, and 26 into the space between the face of the stator 38 and the rotor 42. From this space all of the samples may pass through the single passageway 44 located in the rotor 42 as well as around the rotor 42 into the chamber 54 and therefrom around the annulus of the rotor shaft 36 and out of the duct 12. With the rotor 42 backed away from the stator 38 the ball valve 48 is able to push the slide tube 52 out from the face of the stator 38 and to seal the passageway 40' connected to the sample probe 28. Thus the sample taken by the sample probe 28 is not allowed to exhaust along with the other passageways 40 and does not come into play into any averaging of the remaining sample tubes 20, 22, 24, and 26. The moving of the rotor 42 away from the face of the stator 38 may be accomplished in a number of ways. The rotor shaft 36 may be cammed to retract upon reaching a predetermined angular position. Furthermore a magnetic field may be energized around a magnetic portion of the rotor shaft 36 (not shown) which would draw the rotor shaft 36 into it making it operate like a movable core transformer and causing the backing away of the rotor 42 from the stator 38.

Figure 5:
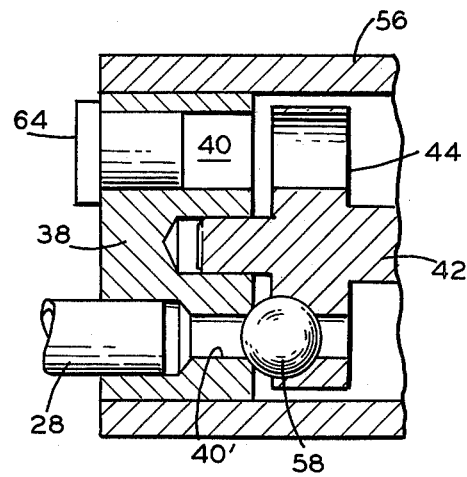
FIG. 5 is an alternate embodiment of the valve mechanism of FIG. 3 displaying a ball valve for switching between individual probes and averaging of samples.

With particular reference to FIG. 5 a mechanical method of backing the rotor 42 away from the stator 38 may also be had. To accomplish this a ball 58 may be fixed at some position along the rotor 42 different from the passageway 44. The ball 58 is sized so as to completely fit into any of the passageways 40 and partially fit into 40' to thereby allow flush contact between the face of the rotor 42 and the stator 38. The ball 58 is positioned along the same diameter as the passageway 44 and is angularly indexed so as to fit into one of the passageways 40 whenever the passageway 44 is aligned with a passageway 40 not entered by the ball 58. A hole 62, which may be seen at FIG. 4 is plugged by a plug 64. The passageway 40' is smaller than any of the passageways 40. Thus when the ball 58 is aligned with the passageway 40', the ball 58 is unable to completely enter into the passageway 40' and causes the rotor 42 to be backed away from the stator 38. This allows all of the passageways 40 with the exception of the passageway 40' connected to sample probe 28 to be exhausted into the space between the rotor 42 and the stator 38 allowing the fluid to pass around the rotor 42, enter into the chamber 54, and to be exhausted around the annulus of the rotor shaft 36.

Certain modifications and improvements will be obvious to persons skilled in the art upon the reading of this specification. It will be understood that all such improvements and modifications have been deleted herein for the sake of conciseness and readability and are intended to be within the scope of the following claims.

What we claim as new and desire to be protected by Letters Patent is:

1. A fluid sampling system for analyzing fluids in a duct conducting fluid therethrough comprising:
    valve means connectable to a fluid analyzer;
    a first sample probe having an inlet located at one point in the duct and an outlet connectable to said valve means and having a single bend of substantially 180° between the inlet and the outlet of said first sample probe; and
    a second sample probe having an inlet located at another point in the duct and an outlet connectable to said valve means, said second sample probe having a length between inlet and outlet substantially identical to the length between inlet and outlet of said first sample probe and also having a single bend of substantially 180° between the inlet and the outlet of said second sample probe to provide substantially identical transport times to fluids conducted through said first and second sample probes from different points in the duct.

2. A fluid sampling system as set forth in claim 1 wherein said valve means includes selection means for allowing individual connection of the outlet of either said first or said second sample probe to the analyzer.

3. A fluid sampling system as set forth in claim 2 wherein said valve means and said selection means is mounted within the duct.

4. A fluid sampling system for analyzing fluids in a duct;
    valve means connectable to a fluid analyzer;
    a first sample probe having an inlet located at one point in the duct and an outlet connectable to said valve means;
    a second sample probe having an inlet located at another point in the duct and an outlet connectable to said valve means, said second sample probe having a length between inlet and outlet substantially identical to the length between inlet and outlet of said first sample probe to provide substantially identical transport times to fluids conducted through said first and second sample probes; and wherein
    said valve means includes selection means for allowing individual connection of the outlet of either said first or said second sample probe to the analyzer with said selection means including a stator having a pair of passageways respectively connected to the outlet of said first and second sample probe and a rotor having a single passageway and being rotatable to have the passageway of the rotor selectively aligned with the pair of passageways of said stator.

5. A fluid sampling system as set forth in claim 4 wherein said rotor is selectively alignable with said stator to block one of the stator passageways while allowing fluid flow between the second passageway of the stator and the passageway of the rotor.

6. A fluid sampling system as set forth in claim 4 wherein said rotor is selectively alignable with said stator to be offset from said stator to allow fluid flow between both of the passageways of said stator and the passageway of said rotor.

7. A fluid sampling system as set forth in claim 1 wherein said first and said second sample probes are substantially equal in diameter to provide substantially equal volumes of sample flow therethrough.

8. A fluid sampling system as set forth in claim 2 including a third sample probe having an inlet located along a wall of the duct and an outlet connected to said valve means.

9. A fluid sampling system as set forth in claim 8 wherein said selection means includes means for connecting the outlet of said third sample probe to the analyzer while blocking the outlets of said first and second sample probes.

* * * * *